United States Patent

Lisowsky

Patent Number: 5,545,785
Date of Patent: Aug. 13, 1996

[54] PROCESS FOR PREPARING BISCYCLOPENTADIENYL COMPOUNDS

[75] Inventor: Richard Lisowsky, Kamen, Germany

[73] Assignee: Witco GmbH, Bergkamen, Germany

[21] Appl. No.: 377,901

[22] Filed: Jan. 25, 1995

[30] Foreign Application Priority Data

Jan. 26, 1994 [DE] Germany .......................... 44 02 192.5

[51] Int. Cl.$^6$ ...................................................... C07C 2/54
[52] U.S. Cl. ........................ 585/375; 585/350; 585/376; 585/446
[58] Field of Search .................................. 585/350, 375, 585/376, 446

[56] References Cited

U.S. PATENT DOCUMENTS

| | | | |
|---|---|---|---|
| 3,036,136 | 5/1962 | Leigh | 260/666 |
| 4,985,576 | 1/1991 | Rohrmann et al. | 556/435 |
| 5,191,132 | 3/1993 | Patsidis et al. | 585/375 |

FOREIGN PATENT DOCUMENTS

| | | |
|---|---|---|
| B-61106/90 | 2/1991 | Australia . |
| 0344887 | 12/1989 | European Pat. Off. . |
| 0351392 | 1/1990 | European Pat. Off. . |
| 0413326 | 2/1991 | European Pat. Off. . |
| 0416815 | 3/1991 | European Pat. Off. . |
| 0420436 | 4/1991 | European Pat. Off. . |
| 0480390 | 4/1992 | European Pat. Off. . |
| 0520732 | 12/1992 | European Pat. Off. . |
| 0530908 | 3/1993 | European Pat. Off. . |
| 3844282 | 7/1990 | Germany . |

OTHER PUBLICATIONS

Chen et al. *Organometallics*, vol. 13, No. 10, 3932–3942 (Oct. 1994).
Duff et al. *Journal of Organometallic Chemistry*, 293, 271–283 (1985).
Eisch et al., *Journal of Organometallic Chemistry*, 296, C27–C31 (1985) (month unknown).
Collins et al., X–Ray structures of ethylenebis (tetrahydroindenyl)–titanium and –zirconium dichlorides: a revision, *J. Organomet. Chem.*, 342:21–29 (1988) (month unknown).
Bandy et al., Polymerisation of Ethylene and Propene using New Chiral Zirconium Derivatives. Crystal Structure of [ZrL$^1$Cl$_2$]–[H$_2$L$^1$=(4S, 5S)–trans–4, 5–bis(1H–inden–1–ylmethyl)–2, 2–dimethyl–1, 3–dioxolane], 1991 *J. Chem. Soc. Dalton Trans.*, 2207–2216.

*Primary Examiner*—Shrive Beck
*Assistant Examiner*—Timothy H. Meeks
*Attorney, Agent, or Firm*—Scully, Scott, Murphy & Presser

[57] ABSTRACT

The invention relates to a process for preparing biscyclopentadienyl compounds of the general formula $$(CpR_a)_2\text{—}Q$$

by reaction of $CpR_a$, in a first step, in accordance with the general equation $$2CpR_a+(R^3R^4)_cMg \rightarrow (CpR_a)_2Mg+cR^3H+cR^4H$$

and further reaction in accordance with the general equation $$(CpR_a)_2Mg+XQX^1 \rightarrow (CpR_a)_2Q+MgXX^1$$

6 Claims, No Drawings

PROCESS FOR PREPARING BISCYCLOPENTADIENYL COMPOUNDS

BACKGROUND OF THE INVENTION

The present invention relates to an improved process for preparing bridged biscyclopentadienyl compounds.

Compounds of this type are starting components for, for example, chiral, stereorigid metallocene compounds which, in combination with cocatalysts, are used, inter alia, as stereospecific catalyst systems of high activity in the polymerization of olefins (EP-A-O 51 392).

There have therefore been many proposals in the past for preparing these bridged biscyclopentadienyl compounds, with the general reaction scheme

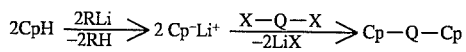

wherein CpH is cyclopentadiene, R is a short-chain alkyl radical, Q is an alkyl or aryl radical, and X is Cl, Br, I or —O—tosyl being largely used. These processes have the disadvantage that they are carried out at temperatures $\leq 70°$ C. using problematical solvents such as ethers, methylene chloride, chloroform or hexamethylenephosphoramide (HMPA). In addition, the yield of biscyclopentadienyl compounds was generally small and was further reduced by purification processes required (Journal of Organometallic Chemistry, 1988, 342, 21–29, DE-A 38 44 282).

It is therefore an object of the present invention to provide a process which makes possible the preparation of bridged biscyclopentadienyl compounds in substantially higher yields and high purity without technically complicated process steps.

This object was surprisingly achieved by reaction of biscyclopentadienylmagnesium compounds $(CpR_a)_2Mg$ with suitable difunctional compounds $XQX^1$.

BRIEF SUMMARY OF THE INVENTION

The subject matter of the invention is accordingly a process for preparing biscyclopentadienyl compounds of the general formula (1)

$$(CpR_a)_2—Q \quad (1)$$

in which Cp can be cyclopentadienyl or indenyl radicals which can be, if desired, singly or multiply substituted, R is alkyl, alkoxy, phosphine, amino, alkylamino, dialkylamino, alkyl, aryl-alkyl, or aryloxy alkyl groups with $0 \leq a \leq 4$, and Q is a single-membered or multi-membered structural bridge between the Cp rings, wherein Q is

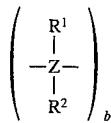

where $R^1$ and $R^2$ are identical or different and each is a hydrogen atom, a $C_1$–$C_{10}$-alkyl group or a $C_6$–$C_{10}$-aryl group and Z is carbon, silicon or germanium and b is 1, 2, or 3, which process is characterized in that, in a first step, the corresponding $CpR_a$ is reacted with one or more magnesium compounds $(R^3R^4)_cMg$, wherein $R^3$ and $R^4$ are each bonded to the Mg and each can be, independently of one another, H or a $C_1$–$C_{12}$-alkyl radical and c is 0 or 1, and, in a second step, the reaction product of the first step is reacted with $QXX^1$, where X and $X^1$ are each bonded to Q and each can be identical or different and each is Cl, Br, I or —O—$SO_2R^5$ wherein $R^5$ is an alkyl radical having 1–10 carbon atoms (such as methyl or ethyl) or an aryl radical having 6–10 carbon atoms (such as phenyl, benzyl or phenethyl).

Referring to the R substituents, each one can be

- alkyl containing 1 to 10 carbon atoms, for example methyl (including dimethyl and trimethyl);
- alkoxy containing 1 to 10 carbon atoms, for example methoxy (including dimethoxy and trimethoxy);
- alkylamino and/or dialkylamino, wherein each alkyl group contains 1 to 10 carbon atoms, for example dimethylamino and dipropylamino (including bis(dimethylamino));
- alkoxyalkyl containing a total of 2 to 20 carbon atoms;
- aryl-alkyl and/or aryloxy-alkyl groups wherein the aryl group contains 6 to 10 carbon atoms and the alkyl portion contains 1 to 10 carbon atoms;
- phosphine, including phosphine substituted with 1 or 2 groups each of which is $C_1$–$C_{10}$ alkyl or $C_6$–$C_{10}$ aryl, for example diphenylphosphino.

DETAILED DESCRIPTION OF THE INVENTION

The compounds of the general formula (1) are prepared by reaction in a first step according to general equation $$2CpR_a + (R^3R^4)_cMg \rightarrow (CpR_a)_2Mg + cR^3H + cR^4H$$

wherein Cp, $R_a$, $R^3$, $R^4$, a and c are as defined above.

The reactions are carried out in an inert gas atmosphere and with exclusion of oxygen and moisture. Here, according to the invention, the components are preferably initially charged at room temperature in an inert solvent and the temperature is increased with vigorous stirring.

Inert solvents which can be used are those customary in this field such as, for example, aliphatic or cyclic ethers or aromatic hydrocarbons.

According to the invention, preference is given to aliphatic hydrocarbons having boiling points $\geq 60°$ C., preferably $\geq 80°$ C., in particular in the range of $80°$–$120°$ C. To achieve practical reaction times, the reaction is preferably carried out at the boiling point of the solvent, in particular between $80°$–$120°$ C. The amount of solvent is largely non-critical. However, to achieve high space time yields it is carried out in the upper technically possible region.

Compounds of the formula $(R^3R^4)_cMg$ used are those in which $R^3$ and $R^4$ are identical or different and are H or $C_1$–$C_{12}$-alkyl radicals and c is 0 or 1, preferably 1. According to the invention, preference is given to butylethylmagnesium, di-n-butylmagnesium, di-n-hexylmgnesium, n-butyl-sec-butylmagnesium in their commercial formulations, or in particular, BOMAG®-A from Witco GmbH (a mixture of dibutylmagnesium, dioctylmagnesium and optionally, butyloctylmagnesium, wherein the ratio of butyl: octyl chains in the overall mixture is about 3:1, 20% strength in heptane). In the case that the one or more compounds $(R^3R^4)_cMg$ are provided in a solvent, no additional solvent is required for carrying out the reaction. The course of the reaction can be monitored by means of the gas evolution.

The $(CpR_a)_2Mg$ compounds thus obtained are, according to the invention, reacted, preferably directly, in a second step, with one or more compounds of the formula X—Q—$X^1$ in accordance with the general reaction equation $$(CpR_a)_2Mg + XQX^1 \rightarrow (CpR_a)_2Q + MgXX^1$$

to give the bridged biscyclopentadienyl compounds.

The components XQX[1] which can be used for bridging include the compounds known from the prior art (EP-A-0 480 390, EP-A-0 413 326, EP-A-0 530 908, EP-A-0 344 887, J. Chem. Soc. Dalton Trans., 19911, 2207). According to the invention, preference is given to compounds in which X and X[1] are Cl, Br or —O—tosyl and Q is —$CH_2$—$CH_2$— or —$Si(CH_3)_2$—.

The reaction mixture of the first step is, if desired, cooled to below its boiling point prior to addition of the component XQX[1] and after addition thereof is complete it is again heated to the boiling point.

If desired, the reaction rate can be increased by additionally using one or more ethers such as, preferably, dialkyl ethers having, in particular, from 6 to 10 carbon atoms such as, in particular, di-n-butyl ether in at most the stoichiometric amount, based on magnesium.

The reaction times are usually between 1 and 3 hours.

In the process of the invention, the starting materials are, in both steps, preferably used in stoichiometric amounts. As a result of the almost quantitative reaction under practical conditions, the bridged biscyclopentadienyl compounds are formed in such purities that they can be used directly, without work up, for further reactions (such as, for example, for the preparation of metallocenes).

Examples of the bridged biscyclopentadienyl compounds which can be prepared by the process of the invention are dimethylsilylbis(1-indene), dimethylsilylbis-(1-cyclopentadiene), 2,2-propylbis(1-indene), 2,2-propylbis(trimethylcyclopentadiene), 2,2-propylbis (5-dimethylamino-1-indene), 2,2-propylbis(6-dipropylamino-1-indene), 2,2-propylbis(4,7-bis(dimethylamino-1-indene)), 2,2-propylbis(5-diphenylphosphino-1-indene), 2,2-propylbis(4,5,6,7-tetrahydro-1-indene), 2,2-propylbis(4-methyl-1-indene), 2,2-propylbis (5-methyl-indene), 2,2-propylbis (6-methyl-1-indene), 2,2-propylbis (7-methyl-1-indene), 2,2-propylbis (5-methoxy-1-indene), 2,2-propyl-bis(4,7-dimethoxy-1-indene), 2,2-propylbis( 2,3-dimethyl-1-indene), 2,2-propylbis( 4,7-dimethyl-1-indene), 2,2-propylbis(9-fluorene), 2,2-propylbis( 1-cyclopentadiene), 2,2-propylbis(1-indene) (1-cyclopentadiene), 2,2-propylbis(1-indene) (9-fluorene), diphenylmethylbis(1-indene), diphenylmethylbis(9-fluorene), diphenylmethylbis(1-cyclopentadiene), diphenylmethyblis(1-indene), diphenylmethylbis(1-indene)(1-cyclopentadiene), diphenylsilylbis (1-indene), diphenylsilylbis(1-cyclopentadiene), diphenylsilylbis(1-indene), diphenylsilylbis(1-indene) (1-cyclopentadiene), ethylenebis-(trimethylcyclopentadiene), ethylenebis( 5-dimethylamino-1-indene), ethylenebis(6-dipropylamino-1-indene), ethylenebis(4,7-bis-(dimethylamino)-1-indene), ethylenebis(5-diphenylphosphino-1-indene), ethylenebis(4,5,6,7-tetrahydro-1-indene), ethylenebis (4-methyl-1-indene), ethylenebis(5-methyl-1-indene), ethylenebis(6-methyl-1-indene), ethylenebis(7-methyl-1-indene), ethylenebis(5-methoxy-1-indene), ethylenebis-( 4,7-dimethoxy-1-indene), ethylenebis(2,3-dimethyl-1-indene), ethylenebis(4,7-dimethyl-1-indene), ethylenebis-(1-cyclopentadiene), and ethylenebis(1-indene).

EXAMPLES

All experiments were carried out with exclusion of oxygen and moisture under nitrogen as inert gas.

Example 1

Preparation of ethylenebis (inden-1-yl)$_2$:

A mixture of 812 ml of BOMAG®-A (0.71 mol; butyloctylmagnesium from Witco GmbH; ratio of butyl:octyl chains was about 3:1; 20% strength in heptane) and 184 ml of indene (90% strength; 1.42 mol) was prepared at room temperature by initially charging the butyloctylmagnesium in a 2 liter glass flask and adding the indene. The mixture was subsequently left to react for 3 hours under reflux, until the cessation of the gas evolution indicated that the reaction was complete.

After cooling to 70° C., 61.2 ml (0.71 mol) of 1,2-dibromoethane and 100 ml of di-n-butyl ether were metered in as a mixture via a dropping funnel.

The mixture was again refluxed for 2 hours, after which GC analysis of the reaction solution indicated quantitative conversion with the formation of 96% of ethyleneindenyl$_2$.

After cooling to room temperature, the precipitated $MgBr_2$ was separated off by means of filtration and the filtrate was evaporated to dryness and recrystallized from methanol.

This gave 167 g of ethylindenyl$_2$ (91% of theory) $^1$H-NMR (CDCl$_3$): (mixture of isomers)
Isomer I: 7.5–7.1 (m, 8H); 6.87 (d, 2H); 6.57 (d, 2H); 3.5 (m (b), 2H); 2.1–1.5 (m, 8H)
Isomer II: 7.6–7.2 (m, 8H); 6.35 (s, 2H); 3.4 (s, 4H); 3.0 (s, 4H).

Example 2

Preparation of ethylenebis (inden-1-yl)$_2$:

a) Without use of di-n-butyl ether 416 ml of BOMAG®-A (20% strength in heptane; 0.364 mol) was initially charged in a 1 liter glass flask and heated to reflux. 85.2 ml of indene (94% strength; 0.73 mol) was then added over a period of 30 minutes via a dropping funnel.

The mixture was refluxed for 6 hours.

31.4 ml of 1,2-dibromoethane (0.364 mol) was added at 60°–70° C. without addition of di-n-butyl ether, which resulted in prolonging of the reaction time so that the mixture had to be allowed to react further for 5 hours under reflux until conversion was complete.

After work up as in Example 1, ethylenebis (inden-1-yl) was obtained in 85% yield (79.9 g).

b) Using ethylene glycol di(p-toluenesulfonate):

10 g of indene (95% strength; 82 mmol) was admixed at room temperature with 34.2 g of BOMAG®-A (20% strength in heptane; 41 mmol) and heated for 4 hours under reflux.

Ethylene glycol di(p-toluenesulfonate) (15.7 g; 97% strength; 41 mmol) and 5.3 g (41 mmol) of di-n-butyl ether were then added at room temperature and the mixture was again stirred for 1.5 hours under reflux. After work up, ethylenebis(inden-1-yl) was obtained in 89% yield (18.9 g).

Example 3

Preparation of bis(inden-1-yl)dimethylsilane:

49.6 ml of indene (95% strength; 0.404 mol) and 50 ml of heptane was initially charged in a 500 ml flask and was admixed over a period of 15 minutes under reflux with 231 ml of BOMAG®-A (20% strength in heptane; 0.202 mol). After refluxing for 3 hours, the mixture was cooled to room temperature.

A mixture of 26.1 g of $Me_2SiCl_2$ (0.202), 35 ml of di-n-butyl ether and 20 ml of hexane was then metered into the reaction solution via a dropping funnel and the mixture was refluxed for 2 hours.

GC analysis of the batch showed quantitative conversion with formation of 94% of $Me_2Si(indenyl)_2$.

Filtration, removal of the solvent and recrystallization from methanol gave 50.2 g (86% of theory) of bis (inden-1-yl)dimethylsilane.

$^1$H-NMR (CDCl$_3$): (mixture of isomers)
Isomer I.): 7.5–7.0 (m, 8H); 6.75 (d, 2H); 6.70 (d, 2H); 3.7 (s, 4H), −0.2 (s, 6H)
Isomer II.): 7.5–7.0 (m, 8H); 6.55 (d, 2H); 6.52 (d,2H); 3.7 (s, 4H), 0.05 (s, 3H); −0.4 s,3H)

Example 4

Use of Further Dialkylmagnesium Compounds:

a) Example 3 was repeated, but using dibutylmagnesium (1 molar in heptane) in place of BOMAG®-A. The refluxing times in the reaction of the dialkylmagnesium were herein increased by 30 minutes in each case. Comparable yields of bis(inden-1-yl)dimethylsilane were achieved (83%; 48.4 g).

b) Example 4 a) was carried out using dihexylmagnesium (1 molar in heptane). Here, too, comparable yields were achieved (87%; 50.8 g)

Comparative Example 5

Preparation of $Me_2Si(indenyl)_2$ Via the Li, Na Derivative of Indene:

If a compound $Me_2Si(indenyl)_2$ is prepared via indenylLi or indenylNa, single to multiple over-alkylation occurs, depending on reaction conditions.

a) $Me_2SiCl_2$ (55.97 g; 0.43 mol) was initially charged in 85 ml of diethyl ether. IndenylLi (105 g; 0.86 mol) in 600 ml of diethyl ether was subsequently added at −70° C. over a period of 4 hours.

After addition was complete, the cooling was removed and the mixture was allowed to come to room temperature (RT). It was stirred for a further 8 hours at RT.

The reaction solution was analyzed by means of gas chromatography (GC) or coupled gas chromatography/mass spectroscopy (GC-MS) and contained:

I.) $Me_2Si(indenyl)_2$: 95%

II.) $Me_2Si(indenyl)_2(Me_2Si(indenyl))$: 5%

III.) $Me_2Si(indenyl)_2(Me_2Si(indenyl))$: —

$Me_2Si(indenyl)$: —

75% of theory of pure product could be isolated.

b) Carrying out the reaction in a similar way to a), but at 20° C., gave:

I.): 90%
II.): 10%
III.): 0.2% c) 58.6 g (0.44 mol) of $Me_2SiCl_2$ was initially charged in 100 ml of diethyl ether and admixed at 0° C. with a solution of 121.6 g of indenylNa (0.88 mol) in 400 ml of THF over a period of 1.5 hours. Analysis of the reaction mixture gave:

I.): 80%
II.): 17%
III.): 2%

After work up and crystallization, 50% of theory of pure $Me_2Si(indenyl)_2$ could be isolated.

d) As a comparison therewith, a batch was reacted according to the process of the invention: to a suspension of indenyl$_2$Mg (102 g; 0.4 mol) in 300 ml of heptane were added 0.4 mol of $Me_2SiCl_2$ (51.6 g), dissolved in 50 ml of hexane and admixed with 0.4 mol of n-butyl$_2$O, at RT. The mixture was subsequently heated immediately to reflux and maintained thereat for 3 hours. Analysis of the reaction solution:

I.): 99%
II.): <0.2%
III.): —

Work up and crystallization gave average yields of greater than 85% of $Me_2Si(indenyl)_2$. If the compound is used further without isolation, the yield is, as a result of work up losses not being present, almost quantitative.

Example 6

Preparation of bis(inden-1-yl)dimethylgermanium:

24 g of BOMAG®-A (20% strength; 28.8 mmol) was initially charged in a 100 ml glass flask and heated to reflux. 7.4 g of indene (90% strength; 57.6 mmol) was then added with subsequent refluxing for 4 hours.

A mixture comprising 5 g of $Me_2GeCl_2$ (28.8 mmol) and 3.7 g of di-n-butyl ether was added at room temperature. This was followed by refluxing for 2 hours.

After work up, 7.9 g of $Me_2Ge(indenyl)_2$ (83% of theory) was isolated.

Example 7

Preparation of $Me_2Si(1,3-butylmethylCp)_2$:

20 g of 1-butyl-3-methylcyclopentadiene (0.147 mmol) was admixed at room temperature with 84 ml of BOMAG®-A (20% strength in heptane; 73.4 mmol).

After refluxing for 3 hours, the mixture was cooled to room temperature.

9.5 g of $Me_2SiCl_2$ (73.4 mmol), 12.7 ml of di-n-butyl ether and 7 ml of hexane were then metered into the reaction solution and the mixture was refluxed for 6 hours. GC analysis of the batch showed quantitative conversion with formation of 85% of $Me_2Si-(1,3-butyl-methylCp)_2$. Filtration, removal of solvent and distillation in a bulb tube gave 16.8 g (70% of theory) of $Me_2Si-(butylmethylCp)_2$. (Molecular weight determined by means of GC-MS: 328)

$^1$H-NMR (CDCl$_3$): (mixture of isomers) 6.2–5.8 (m, H—C=C); 3.3–2.9 (m, H—C—C=C—); 2.5–2.3 (m, —CH$_2$—); 2.15–1.95 (m, —CH$_3$); 1.6–1.25 (m, —CH$_2$CH$_2$—); 1.0–0.85 (m, —CH$_3$); 0.15–0.25 (m, H$_3$C—Si).

What is claimed is:

1. A process for preparing a biscyclopentadienyl compound of the general formula (1)

$(CpR_a)_2$—Q 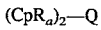 (1)

in which each Cp is a cyclopentadienyl or an indenyl radical; each R is selected from the group consisting of alkyl, phosphine, amino, alkylamino, dialkylamino, alkoxy-alkyl, aryl-alkyl and aryl-oxy-alkyl groups; $0 \leq a \leq 4$; and Q is a single-membered or multi-membered structural bridge between the Cp rings, wherein Q has the formula

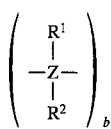

wherein $R^1$ and $R^2$ are identical or different and each is a hydrogen atom, a $C_1$–$C_{10}$-alkyl group or $C_6$–$C_{10}$-aryl group; Z is carbon, silicon or germanium; and b is 1, 2, or 3; wherein the process comprises (a) reacting a compound of the formula $CpR_a$ with one or more magnesium compounds of the formula $(R^3R^4)_c Mg$, wherein $R^3$ and $R^4$ are each bonded to the Mg and each is, independently of one another, H or a $C_1$–$C_{12}$-alkyl radical and wherein c is 0 or 1, under conditions effective to form a compound of the formula $(CpR_a)_2Mg$; and, in a second step, (b) reacting said compound of formula $(CpR_a)_2Mg$ with one or more compounds of the formula $QXX^1$, wherein X and $X^1$ are identical or different and each is Cl, Br, I or —O—$SO_2R^5$ wherein $R^5$ is an alkyl radical having 1 to 10 carbon atoms or an aryl radical having 6–10 carbon atoms, under conditions effective to form said compound of formula (1).

2. A process according to claim 1, wherein the group $(R^1$—Z—$R^2)_b$ is an ethylene radical or an $R^1$—$SiR^2$ group wherein $R^1$ and $R^2$ are identical or different and each is a —$CH_3$, —$C_2H_5$ or phenyl radical.

3. A process for preparing a biscyclopentadienyl compound according to claim 1, wherein steps (a) and (b) are carried out in solvent selected from the group consisting of petroleum ether, heptane, octane, toluene and xylene.

4. A process for preparing a biscyclopentadienyl compound according to claim 1, wherein said one or more magnesium compounds are selected from the group consisting of compounds of the formula $(R^3R^4)_c Mg$ wherein c is 1 and $R^3$ and $R^4$ are identical or different and each is —$C_2H_5$, —$C_4H_9$, —$C_6H_{13}$ or —$C_8H_{17}$, and mixtures of said compounds.

5. A process for preparing a biscyclopentadienyl compound according to claim 4, wherein $(R^3R^4)_c Mg$ is a mixture of compounds wherein c is 1 and each $R^3$ and $R^4$ is n-butyl or n-octyl wherein the ratio of n-butyl substituents to n-octyl substituents in said $(R^3R^4)_c Mg$ is 3:1.

6. A process for preparing a biscyclopentadienyl compound according to claim 1, further comprising, carrying out said second step (b) in the presence of at most the stoichiometric amount, based on magnesium, of one or more dialkyl ethers containing 6 to 10 carbon atoms.

* * * * *

UNITED STATES PATENT AND TRADEMARK OFFICE
CERTIFICATE OF CORRECTION

PATENT NO. : 5,545,785
DATED : August 13, 1996
INVENTOR(S) : Richard Lisowsky

It is certified that error appears in the above-indentified patent and that said Letters Patent is hereby corrected as shown below:

Column 1, line 12: "51" should read --351--

Column 1, line 60: " $C_6$ -$C_{10}$ " should read -- $C_6$ -$_{10}$ --

Column 3, line 28: "dimethylsilylbis-(1" should read --dimethylsilylbis(1 --

Column 3, line 35: " (5-methyl-indene) " -- (5-methyl-1-indene) --

Signed and Sealed this

Twenty-seventh Day of May, 1997

Attest:

BRUCE LEHMAN

Attesting Officer

Commissioner of Patents and Trademarks